US010435099B2

(12) United States Patent
Chen

(10) Patent No.: US 10,435,099 B2
(45) Date of Patent: *Oct. 8, 2019

(54) PERSONAL EXERCISE MEASURING SAFETY SYSTEM

(71) Applicant: Bion Inc., New Taipei (TW)

(72) Inventor: Yi-Lun Chen, New Taipei (TW)

(73) Assignee: BION INC., New Taipei (TW)

( * ) Notice: Subject to any disclaimer, the term of this patent is extended or adjusted under 35 U.S.C. 154(b) by 999 days.

This patent is subject to a terminal disclaimer.

(21) Appl. No.: 14/941,200

(22) Filed: Nov. 13, 2015

(65) Prior Publication Data

US 2016/0144916 A1 May 26, 2016

(30) Foreign Application Priority Data

Nov. 24, 2014 (TW) .............................. 103140585 A

(51) Int. Cl.
| | |
|---|---|
| *G08G 1/16* | (2006.01) |
| *B62J 6/00* | (2006.01) |
| *H04M 1/725* | (2006.01) |
| *A61B 5/11* | (2006.01) |
| *A61B 5/00* | (2006.01) |

(Continued)

(52) U.S. Cl.
CPC ................ *B62J 6/00* (2013.01); *G08G 1/166* (2013.01); *H04M 1/72522* (2013.01); *A61B 5/02438* (2013.01); *A61B 5/11* (2013.01); *A61B 5/6895* (2013.01); *B62J 2099/0013* (2013.01); *H04M 1/7253* (2013.01)

(58) Field of Classification Search
CPC ........ B62J 6/00; G08G 1/166; A63B 24/0062; A63B 24/0003; A63B 71/00; A63B 71/06; A63B 24/00; H04M 1/72522

USPC ...... 340/427, 432, 933, 937; 348/148; 482/8
See application file for complete search history.

(56) References Cited

U.S. PATENT DOCUMENTS

| | | | | |
|---|---|---|---|---|
| 7,714,704 | B1 * | 5/2010 | Mellen ...................... | B60R 1/00 340/425.5 |
| 8,643,722 | B2 * | 2/2014 | Solida ...................... | B62J 99/00 348/148 |

(Continued)

FOREIGN PATENT DOCUMENTS

| | | |
|---|---|---|
| TW | 581016 | 3/2004 |
| TW | I289659 A | 5/2008 |

(Continued)

*Primary Examiner* — Hung T Nguyen
(74) *Attorney, Agent, or Firm* — Chun-Ming Shih

(57) ABSTRACT

A personal exercise measuring safety system is provided. Aforementioned system is applied in a bicycle and includes an image acquiring or information transmitting device, an exercise measuring device, a personal mobile digital measuring device and a power supply device. The image acquiring or information transmitting device is configured on one portion of the bicycle by a fixator. The personal mobile digital measuring device electrically connected with the image acquiring or information transmitting device by a digital image transmitting device so as to receive an image or information. The personal mobile digital measuring device selectively displays the image or information, or provides an external handheld communication device for receiving and displaying the image or information. The power supply device is configured to provide power to each device.

10 Claims, 5 Drawing Sheets

(51) Int. Cl.
*A61B 5/024* (2006.01)
*B62J 99/00* (2009.01)

(56) References Cited

U.S. PATENT DOCUMENTS

| | | | |
|---|---|---|---|
| 2010/0035726 A1* | 2/2010 | Fisher | A63B 24/0084 482/8 |
| 2014/0038781 A1* | 2/2014 | Foley | A63B 24/0075 482/9 |
| 2016/0073722 A1* | 3/2016 | Eustace | A42B 3/0466 340/539.13 |

FOREIGN PATENT DOCUMENTS

| | | |
|---|---|---|
| TW | M446381 U1 | 2/2013 |
| TW | M476291 U | 4/2014 |

* cited by examiner

PERSONAL EXERCISE MEASURING SAFETY SYSTEM

BACKGROUND OF THE INVENTION

This application claims priority benefit of TW Patent Application Ser. No. 103140585 filed 2014 Nov. 24 which is hereby incorporated herein by reference its entirety.

1. Field of the Invention

The present invention relates to a personal exercise measuring safety system, and more particularly, to a personal exercise measuring safety system using image recognition technique to analyze the environment when riding a bicycle.

2. Description of the Prior Art

Riding a bicycle has become a trend for many reasons such as sport and travel and has thus attracted more people to take part in it. However, in a crowded metropolitan area, riding a bicycle on the same road with other vehicles can be dangerous when there is heavy traffic.

A bicycle rider often needs to turn his/her head around to see if there is any vehicle approaching and to keep a safe distance. When turning around, the rider could often fail to notice any obstacles or vehicles ahead, and could encounter some dangerous situation when a reckless driver cuts in the same lane.

Besides, it takes a lot of effort to ride a bicycle under various circumstances, especially under a high-temperature condition. In such case, if no proper measure is taken to evaluate the environment and to monitor the health condition of the rider, the rider could be harmed from excessive bicycle riding.

In addition, prior art bicycle meters disclosed in patents such as Taiwan Patent No. I289659 titled "Intelligent Meter", Taiwan Patent No. 581016 titled "Cycling Computer Device" do not provide images regarding the riding environment. Although Taiwan Patent No. M446381 titled "Monitoring system for bicycle riding behavior" and Taiwan Patent No. M476291 titled "Multifunctional Intelligent Meter" did provide images on the meters, they fail to include environmental images for the rider to observe the environment and alarming information regarding various bicycle riding situations. Therefore, it is necessary to provide a personal exercise measuring safety system which can prompt the bicycle rider with the traffic condition around the rider and alarming information based on current conditions.

SUMMARY OF THE INVENTION

To solve the previous technical problems, one objective of the present application is providing a personal exercise measuring safety system which can use image recognition technique to analyze the environment when riding a bicycle.

To achieve the aforementioned objective, the present application provides a personal exercise measuring safety system. The personal exercise measuring safety system is applied in a bicycle and includes an image acquiring or information transmitting device, an exercise measuring device, a personal mobile digital measuring device and a power supply device. The image acquiring or information transmitting device is configured on one portion of the bicycle by a fixator. The exercise measuring device detects a motion so as to provide a piece of exercise information. The personal mobile digital measuring device is electrically connected with the image acquiring or information transmitting device by a digital image transmitting device so as to receive an image or information. The personal mobile digital measuring device selectively displays the image or information, or provides an external handheld communication device for receiving and displaying the image or information. The digital image transmitting device is a wired or a wireless transmission module. The personal mobile digital measuring device is connected with the exercise measuring device so as to receive and display the exercise information. The power supply device is configured to provide power to the image acquiring or information transmitting device, the exercise measuring device, and the personal mobile digital measuring device.

As above described, the personal exercise measuring safety system acquires rear images from the image acquiring or information transmitting device configured on the back of the bicycle and provides information regarding the rear conditions to the rider. Therefore, the bicycle rider can obtain the real-time information of the rear environment without turning his/her head around when riding.

BRIEF DESCRIPTION OF THE DRAWINGS

For a better understanding of the aforementioned embodiments of the invention as well as additional embodiments thereof, reference should be made to the Description of Embodiments below, in conjunction with the following drawings in which like reference numerals refer to corresponding parts throughout the figures.

DETAILED DESCRIPTION OF THE PREFERRED EMBODIMENT

The following description is about embodiments of the present invention; however it is not intended to limit the scope of the present invention.

Figure 1:
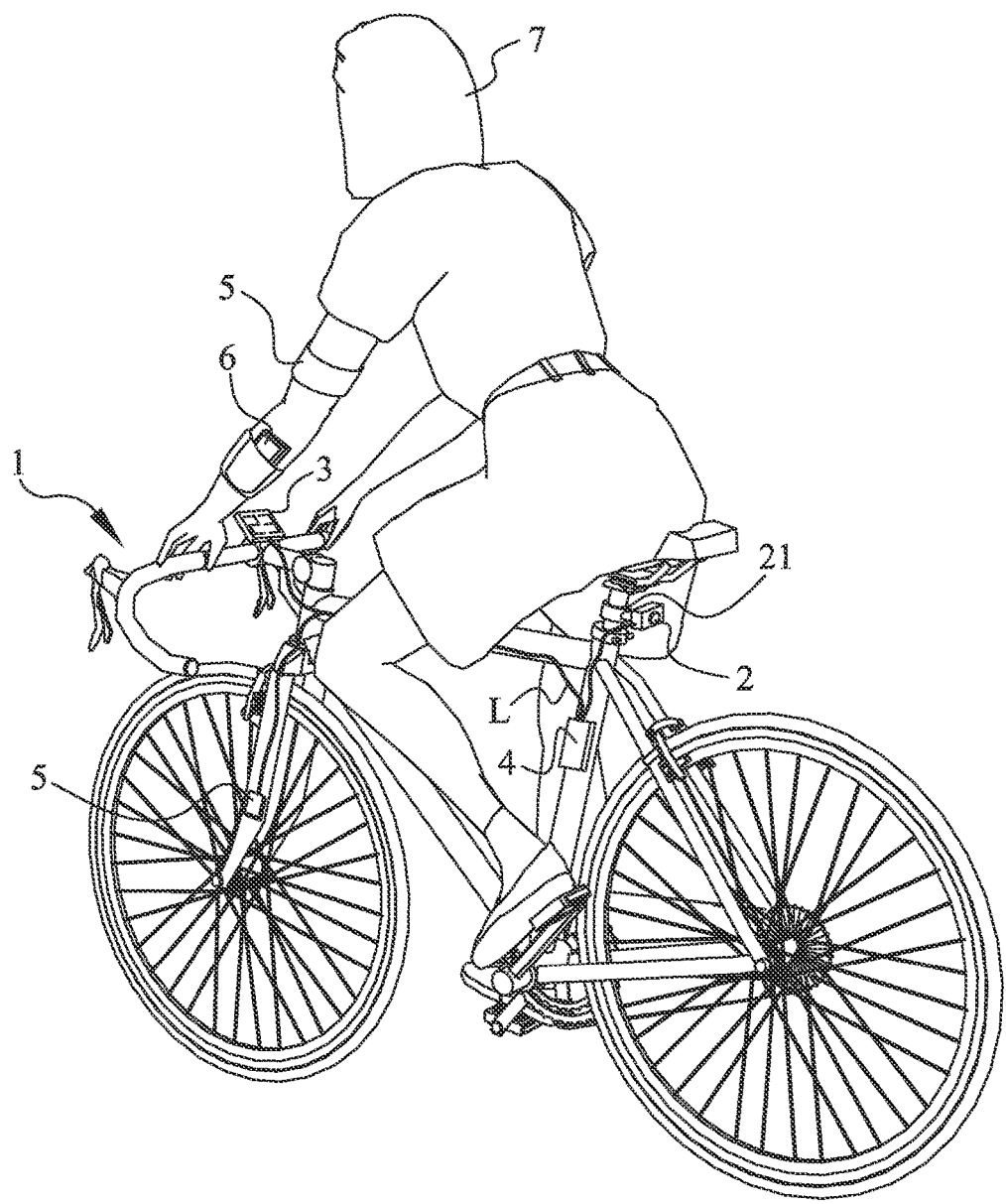
FIG. 1 illustrates a view of a personal exercise measuring safety system of the present invention.

Please refer to FIG. 1 for the personal exercise measuring safety system of the present invention. The personal exercise measuring safety system is applied in a bicycle 1. The personal exercise measuring safety system comprises an image acquiring or information transmitting device 2, a personal mobile digital measuring device 3, a power supply device 4, and an exercise measuring device 5. The image acquiring or information transmitting device 2 is configured on one portion of the bicycle by a fixator 21. The personal mobile digital measuring device 3 is electrically connected with the image acquiring or information transmitting device 2 by a digital image transmitting device so as to receive an image or information. The personal mobile digital measuring device 3 selectively displays the image or information, or to transmit to an external handheld communication device 6 for receiving and displaying the image or information. The personal mobile digital measuring device 3 is further connected with the exercise measuring device 5 so as to receive and display the exercise information. The power supply device 4 is configured to provide power to the image acquiring or information transmitting device 2, the exercise measuring device 5, and the personal mobile digital measuring device 3 through a power cord L. The power supply device 4 can be installed in each one of the devices respectively, or is provided in a form of a battery set of the bicycle.

Figure 2A:
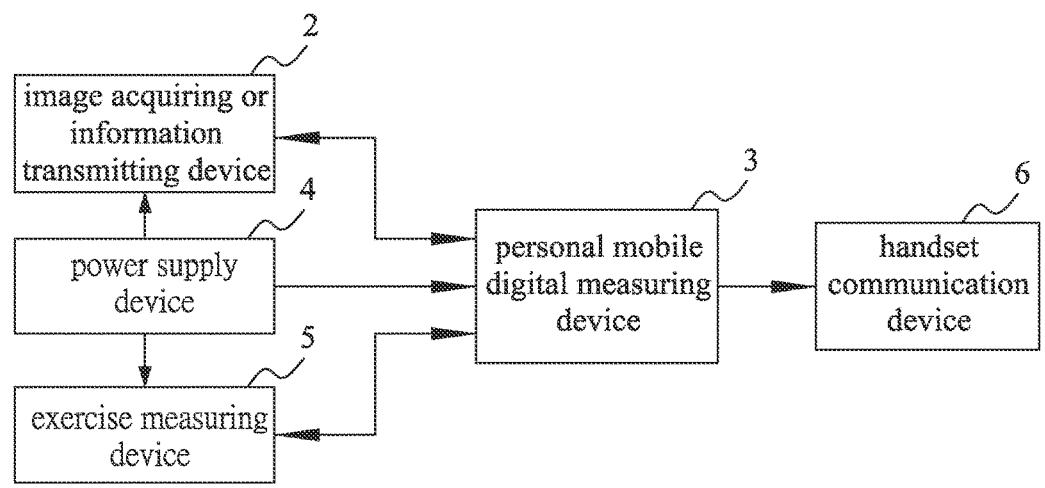
FIG. 2A illustrates a view of a first embodiment of the present invention.

Please refer to both FIG. 1 and FIG. 2A for the first embodiment of the present invention. In the first embodiment, the personal mobile digital measuring device 3 is a cycling computer device and is connected with the image acquiring or information transmitting device 2 (such as a CCD image acquiring or information transmitting device) through wireline or wireless transmission means (such as Wi-Fi, Bluetooth) to acquire the image or information. The personal mobile digital measuring device 3 is further wirelessly connected with the exercise measuring device 5 (such as smart watch, sphygmomanometer, blood glucose meter, thermometer, heart rate monitor strap, or wearable heart rate monitoring device) to obtain the exercise information containing physiological information; the personal mobile digital measuring device 3 is also connected with the exercise measuring device 5 disposed on the bicycle 1 to obtain speed information.

The personal exercise measuring safety system further comprises an environment sensor (such as thermometer, hygrometer, barometer, etc.). The environment sensor is wirelessly connected with the personal mobile digital measuring device 3 and provides a environment sensing information, wherein the personal mobile digital measuring device 3 receives the environment sensing information from the environment sensor, and evaluating a condition of a user 7 by the environment sensing information and the exercise information to determine whether the physical state of the user 7 is suitable for further riding. For example, the personal mobile digital measuring device 3 can determine if there is a risk of heat stroke by obtaining and evaluating the body temperature of the user, the current ambient temperature, and humidity; if so, then the personal mobile digital measuring device 3 can display heat stroke alarming information to remind the user 7.

Figure 3A:
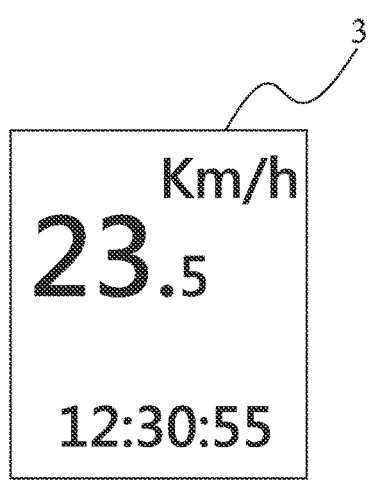
FIG. 3A illustrates a view of the display of the first and third embodiment of the present invention.

Before riding the bicycle 1, the user 7 can place the personal mobile digital measuring device 3 at the bicycle stem and the image acquiring or information transmitting device 2 at the rear of the bicycle. When the user 7 starts to ride the bicycle, the personal mobile digital measuring device 3 can display the current speed of the bicycle 1 through a display module 32 (FIG. 3A) and transmit the real time traffic image to the handheld communication device 6 of the user 7 for display.

Figure 4:
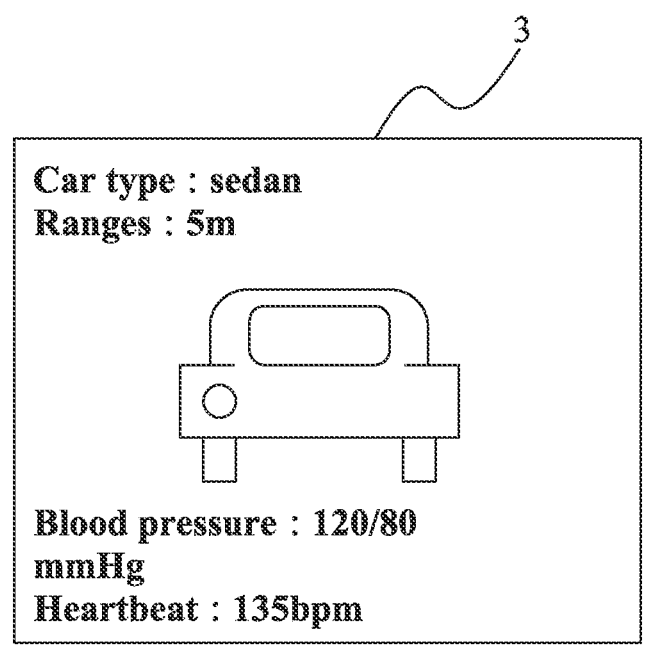
FIG. 4 illustrates a view of the image recognized by the personal exercise measuring safety system

Please refer to FIG. 4, the image acquiring or information transmitting device 2 acquires images from the rear and transmits the images to the personal mobile digital measuring device 3. The personal mobile digital measuring device 3 receives the images and then transmits the images to the handheld communication device 6 for the latter to use the image recognition technique to determine the type of the vehicle (small sedan, motorcycle, or truck) and the distance so as to offer alarming information. For example, when the handheld communication device 6 determines a sedan is coming up fast from the rear and quickly closing the distance with the bicycle 1, it will generate alarming information; when the handheld communication device 6 determines a big truck is approaching, it will generate alarming information to remind the user 7 to keep safe distance.

Figure 2B:
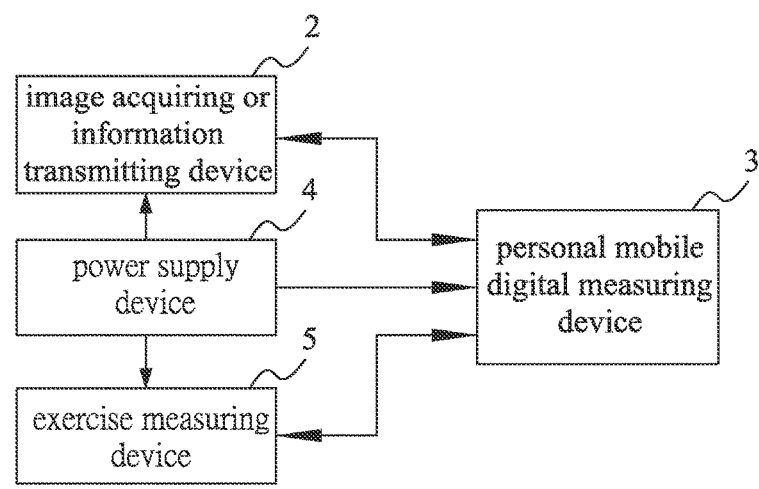
FIG. 2B illustrates a view of a second embodiment of the present invention.
Figure 3B:
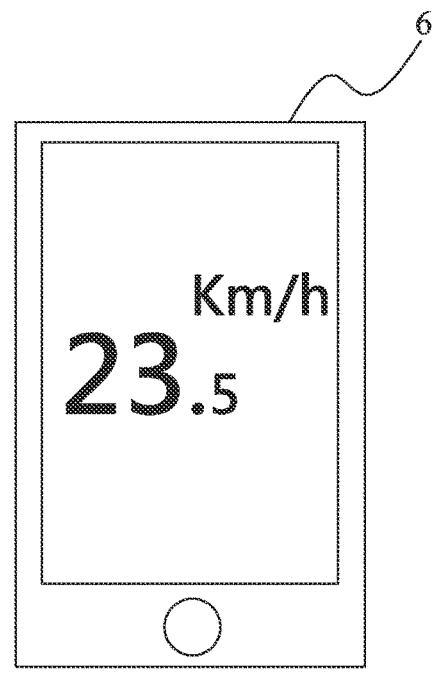
FIG. 3B illustrates a view of the display of the second embodiment of the present invention.

Please refer to FIG. 2B for the second embodiment of the present invention. The second embodiment is different from the first embodiment in that the personal mobile digital measuring device 3 of the second embodiment is a mobile communication device. The mobile communication device is wirelessly connected with the image acquiring or information transmitting device 2, the power supply device 4, and the exercise measuring device 5; and the mobile communication device can directly display the acquired physiological information, speed information, and traffic images (Please refer to FIG. 3B and FIG. 4) and processing the images with the image recognition technique.

Figure 2C:
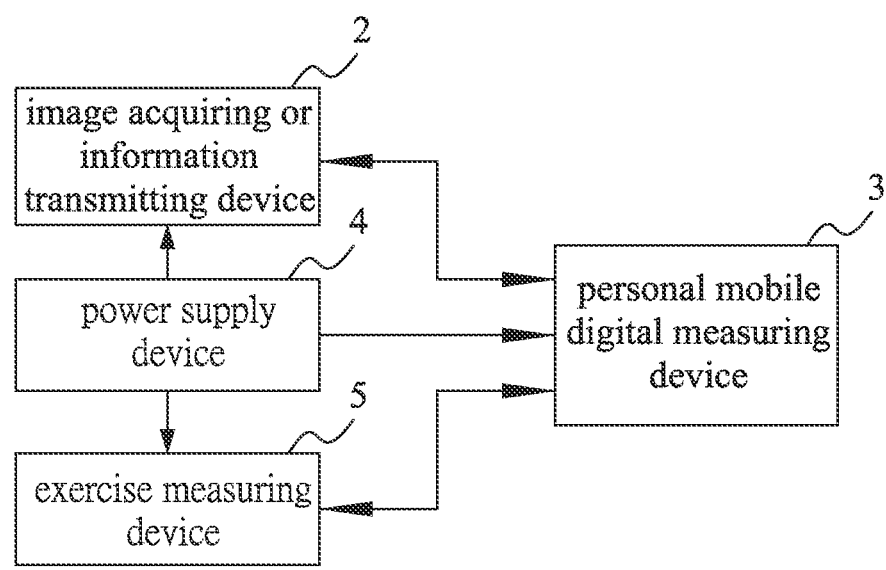
FIG. 2C illustrates a view of a third embodiment of the present invention.

Please refer to FIG. 2C for the third embodiment of the present invention. The third embodiment is different from the first embodiment in that the personal mobile digital measuring device 3 of the third embodiment is a cycling computer device which can display the acquired physiological information, speed information, and traffic images (Please refer to FIG. 3A) and process the images with the image recognition technique. In this embodiment, the personal mobile digital measuring device 3 is connected with the image acquiring or information transmitting device 2, the power supply device 4, and the exercise measuring device 5 through wired or wireless means.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A personal exercise measuring safety system applied in a bicycle, comprising:
    an image acquiring or information transmitting device configured on one portion of the bicycle by a fixator;
    an exercise measuring device for detecting a motion so as to provide a piece of exercise information; and
    a personal mobile digital measuring device, connected with the image acquiring or information transmitting device by a digital information transmitting device so as to receive an image or to transmit information, wherein the personal mobile digital measuring device selectively displays the image or the information, or to transmit to an external handheld communication device to display the image or the information, wherein the digital image transmitting device is a wired or a wireless transmission module, the personal mobile digital measuring device is further connected with the exercise measuring device so as to receive and display the exercise information; and a power supply device connected with the image acquiring or information transmitting device, the exercise measuring device, and the personal mobile digital measuring device so as to provide power thereto.

2. The system as claimed in claim 1, wherein the personal mobile digital measuring device is a cycling computer device.

3. The system as claimed in claim 1, wherein the personal mobile digital measuring device is a mobile communication device.

4. The system as claimed in claim 1, wherein a display module of the personal mobile digital measuring device is configured to display the image or the information.

5. The system as claimed in claim 1, wherein the personal mobile digital measuring device is further connected with a handheld communication device, and provides the handheld communication device to display the image or the information.

6. The system as claimed in claim 1 further comprising an environment sensor connected with the personal mobile digital measuring device, wherein the personal mobile digital measuring device receives environment sensing information from the environment sensor, and evaluating a condition of a user by the environment sensing information and the exercise information.

7. The system as claimed in claim 1, wherein the personal mobile digital measuring device is a cycling computer device which is able to display information.

8. The system as claimed in claim 1, wherein the exercise information comprises speed information, wheel rotation speed information, or physiological information.

9. The system as claimed in claim 1, wherein a personal mobile digital measuring device further determines an environmental condition so as to provide alarming information according to the image or the information.

10. The system as claimed in claim 1, wherein the power supply device can be installed in each one of the devices respectively, or is provided in a form of a battery set of the bicycle.

* * * * *